US00PP27834P2

(12) United States Plant Patent
Hansen

(10) Patent No.: US PP27,834 P2
(45) Date of Patent: Apr. 4, 2017

(54) ***BUDDLEIA* PLANT NAMED 'DARK DYNASTY'**

(50) Latin Name: *Buddleia davidii*
Varietal Denomination: Dark Dynasty

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 149 days.

(21) Appl. No.: 14/545,727

(22) Filed: Jun. 10, 2015

(51) Int. Cl.
*A01H 5/00* (2006.01)

(52) U.S. Cl.
USPC ..... Plt./242

(58) Field of Classification Search
USPC ..... Plt./226, 242
See application file for complete search history.

(56) References Cited

U.S. PATENT DOCUMENTS

| | | | |
|---|---|---|---|
| PP12,383 | P2 | 2/2002 | Dransfield |
| PP14,370 | P2 | 12/2003 | Turrell |
| PP17,332 | P2 | 1/2007 | Moore |
| PP19,934 | P2 | 4/2009 | Davis |
| PP19,935 | P2 | 4/2009 | Bloom |
| PP19,950 | P3 | 4/2009 | Werner |
| PP19,991 | P3 | 5/2009 | Werner |
| PP22,063 | P2 | 8/2011 | Valin |
| PP22,064 | P2 | 8/2011 | Valin |
| PP22,065 | P2 | 8/2011 | Podaras |
| PP22,066 | P2 | 8/2011 | Podaras |
| PP22,067 | P2 | 8/2011 | Podaras |
| PP22,068 | P2 | 8/2011 | Podaras |
| PP22,069 | P2 | 8/2011 | Podaras |
| PP22,080 | P2 | 8/2011 | Podaras |
| PP22,081 | P2 | 8/2011 | Podaras |
| PP22,098 | P2 | 8/2011 | Podaras |
| PP22,108 | P2 | 9/2011 | Podaras |
| PP22,109 | P2 | 9/2011 | Podaras |
| PP22,110 | P2 | 9/2011 | Podaras |
| PP22,142 | P2 | 9/2011 | Podaras |
| PP22,143 | P2 | 9/2011 | Podaras |
| PP22,144 | P2 | 9/2011 | Podaras |
| PP22,177 | P2 | 10/2011 | Podaras |
| PP22,367 | P2 | 12/2011 | Podaras |
| PP22,465 | P2 | 1/2012 | Brand |
| PP22,680 | P2 | 4/2012 | Senior |
| PP23,214 | P2 | 11/2012 | Moore |
| PP23,425 | P2 | 2/2013 | Werner et al. |
| PP23,461 | P2 | 3/2013 | Valin |
| PP23,462 | P2 | 3/2013 | Valin |
| PP23,463 | P2 | 3/2013 | Valin |
| PP23,464 | P2 | 3/2013 | Valin |
| PP23,498 | P2 | 3/2013 | Podaras |
| PP24,015 | P3 | 11/2013 | Werner |
| PP24,016 | P3 | 11/2013 | Werner |
| PP24,030 | P3 | 11/2013 | Podaras |

*Primary Examiner* — Susan McCormick Ewoldt
*Assistant Examiner* — Karen Redden

(57) ABSTRACT

*Buddleia* 'Dark Dynasty' is a short, compact, mounded, multi-stemmed, winter-hardy butterfly bush with long, compact, flowering, thyrse over a long season beginning mid-summer with sweetly-fragrant royal-purple flowers that are attractively offset by dark green foliage.

1 Drawing Sheet

Botanical classification: *Buddleia davidii.*
Variety denomination: 'Dark Dynasty'.

BACKGROUND OF THE PLANT

The present invention relates to the new and distinct butterfly bush plant, *Buddleia* 'Dark Dynasty' hybridized by Hans A. Hansen in the summer of 2011 at a wholesale perennial nursery in Zeeland, Mich., USA. 'Dark Dynasty' is the result of an ongoing breeding program conducted by the inventor. The goals for this program have been to produce improved, garden-worthy plants for the ornamental plant market. The new plant, originally assigned breeder code H11-12-08, is a single seedling selected from an open-pollination of the unreleased proprietary hybrid HK10-08-01 (not patented) as the female or seed patent. The male parent is unknown, and the area where the female parent was grown was heavily planted in many other selected proprietary hybrids of *Buddleia*, so the opportunity for diversity was great.

*Buddleia* 'Dark Dynasty' was first asexually propagated from a single select plant in 2012 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

The following traits have been repeatedly observed and are determined to be the unique characteristics of 'Dark Dynasty'. There are no dark purple flowering butterfly bushes known to the inventor with the compact habit of 'Dark Dynasty'.

The nearest comparison plants are *Buddleia* 'Black Knight' (not patented) and *Buddleia* 'Blue Chip Jr' U.S. Plant Pat. No. 26,581. 'Black Knight' is much taller and wider in habit than 'Dark Dynasty'. 'Blue Chip Jr' is slightly smaller in height and width with a lighter colored flower of lavender compared with the royal purple of 'Dark Dynasty'. 'Purple Haze' (U.S. Plant Pat. No. 24,514) is lighter in flower color and much broader in habit than 'Dark Dynasty'. 'Nanho Blue' (not patented), 'Violet Blue' (not patented) and 'Potter's Purple' (not patented) are all lighter in flower color and much larger in habit than 'Dark Dynasty'. 'Purple Emperor' (not patented) is similar in the darkness of the flower, but the habit is much larger than the new plant.

The following Table 1 further demonstrates some comparisons with the new plant and the nearest comparison cultivars.

TABLE 1

| CULTIVAR | FLOWER COLOR | HABIT | SIZE (H × W) |
|---|---|---|---|
| 'Dark Dynasty' | royal purple | compact mound | 115 cm × 110 cm |
| 'Black Knight' | deep purple-blue | upright spreading | 200 cm × 165 cm |
| 'Purple Haze' | med. violet | spreading mound | 90 cm × 150 cm |
| 'Blue Chip Jr' | lavender | short mound | 90 cm × 90 cm |
| 'Nanho Blue' | mauve blue | upright mound | 140 cm × 145 cm |
| 'Violet-blue' | lavender | sprawling mound | 150 cm × 165 cm |
| 'Potter's Purple' | med. violet | large mound | 190 cm × 190 cm |
| 'Purple Emperor' | purple | upright | 150 cm × 150 cm |

*Buddleia* 'Dark Dynasty' is a unique winter-hardy butterfly bush different from all other *Buddleia* cultivars known to the inventor based on the following combined traits:

1. Winter-hardy shrub, with multiple-stemmed, branched, compact, rounded-mounded habit.
2. Many-flowered compact thyrse over a prolonged season beginning mid-summer.
3. Dark flowers of royal purple petals.
4. Lanceolate foliage of dark green with silvery undersides.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
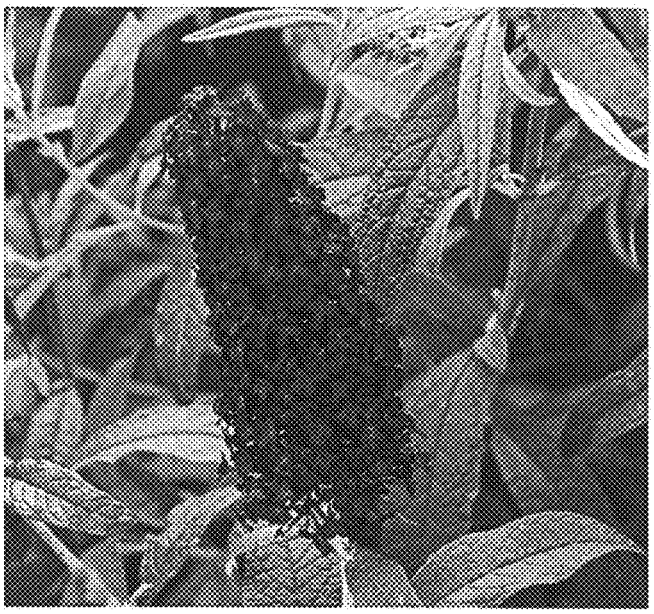
FIG. 1 shows a close-up of the flowers.
Figure 2:
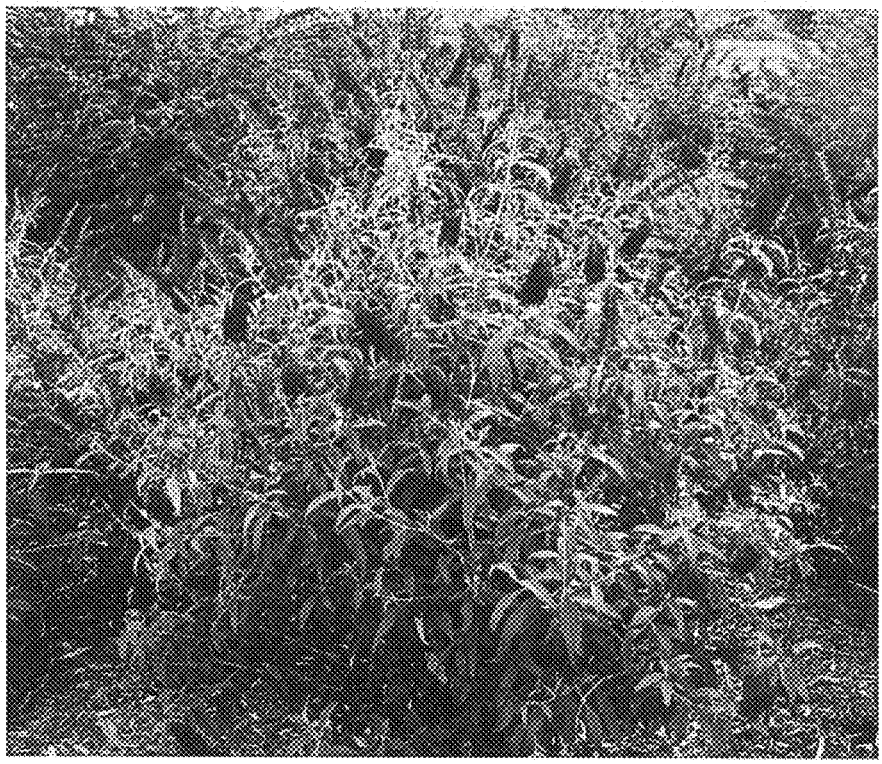
FIG. 2 shows the habit of a three-year-old plant in mid-season flowering.

The following descriptions and color references are based on the 2001 edition of The Royal Horticultural Society Colour Chart except where common dictionary terms are used. The new plant, *Buddleia* 'Dark Dynasty', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in fall or early spring to promote new growth and flowering.

Parentage: Proprietary hybrid HK10-08-01 (not patented) as the female or pod parent times an unknown open-pollination as the male or pollen parent.

Propagation:

*Method*.—Softwood cuttings.

*Time to initiate roots from tissue culture*.—About two weeks.

*Rooting habit*.—Normal, dense and thick at base to about 1.5 cm diameter; fibrous, branching.

*Root color*.—Creamy white between RHS 159A and lighter than RHS 159 D depending on soil type.

*Crop time*.—Under normal summer growing conditions 12 to 15 weeks to flower in a four-liter container from cutting. Plant vigor is very good.

Plant description:

*Plant shape and habit*.—Winter-hardy, herbaceous, semi-woody, well-branched shrub with about 15 thick upright and branched main stems producing a compact rounded mound about 115 cm tall and about 110 cm wide; width of plant about 120 cm.

*Stem*.—Rounded and woody in lower portion rounded in cross section with exfoliating bark; younger upper portion puberulent and quadrangular in cross section with ridges in corners; strong and flexible; average about 85 cm tall from soil line to just below terminal flowers, and about 1.2 cm diameter at the base; before distal flowers about 12 branches per main stem extending at about 45° to 35° angle from horizontal.

*Stem color*.—Distal portion just below flowers nearest RHS 191D with ridges between RHS N187A and RHS N187B, and in about basal 10 cm between RHS 200C and RHS 165B with striations between RHS 200A and RHS N199B.

*Plant size*.—Unpinched plant with stems flowering to about 115 cm tall; overall plant about 110.0 cm wide.

*Internode*.—About 12 nodes per stem below flowers, average internode length about 7.0 cm on unpinched plant; upper internodes slightly more elongated than lower internodes.

Foliage description: Opposite, decussate; serrulate; puberulent abaxial and glabrous adaxial; elliptic to lanceolate with attenuate base and acute apex; no foliar fragrance detected.

*Leaf blade size*.—Up to about 13.0 cm long and about 7.0 cm wide, average about 12.5 cm long and about 5.5 cm wide; becoming smaller in distal portion of stem.

*Foliage color*.—Young expanding leaf adaxial side lighter than RHS N138D and less gray than RHS 191C, young expanding abaxial nearest RHS 192C; mature leaves adaxial side nearest RHS 139A and abaxial between RHS 191C and RHS N138D.

*Veins*.—Reticulate; abaxial raised, adaxial slightly impressed.

*Vein color*.—Young expanding adaxial center main vein nearest RHS 192D and lateral veins nearest RHS 136B, abaxial young expanding veins nearest RHS 192D; mature adaxial variable main vein nearest RHS 138C lateral veins nearest RHS 139A; abaxial main center and lateral vein between RHS 146B and RHS 147C.

*Petioles*.—Glaucous and glabrous adaxial, pubescent abaxial; flatted partially top to bottom; average size about 0.5 cm long and about 2.0 mm wide at the point of attachment to stem.

*Petiole color*.—Nearest RHS 192C and RHS 145C.

*Inflorescence description*.—Glomerate thyrse consisting of about 600 self-cleaning salverform flowers; to about 27.5 cm long and about 10.0 cm across; beginning in mid-July and continuing until late October in Michigan.

*Buds*.—Narrowly spatulate, apex rounded; one day prior to opening about 12.0 mm long and about 4.0 mm diameter in club and throat about 1.0 mm diameter in throat and about 8.0 mm long.

*Bud color*.—Nearest RHS N79A in club portion and tube portion between RHS 70A and RHS 70B; buds about three days from opening nearest RHS 71A in tube and unopened club portion nearest RHS N187A.

*Sepals*.—Typically four, proximal two-thirds connate, adpressed to corolla tube; acute apex; glabrous adaxial and pubescent abaxial; margin entire, edentate; fused in about the basal 1.6 mm and split in about the terminal 0.9 mm; forming a corolla about 2.5 mm long and about 1.0 mm across; individually less than about 1.0 mm wide at point of fusion.

*Sepal color*.—Adaxial nearest RHS 138C, abaxial between RHS 145A and RHS 139C heavily tinted with nearest RHS N187A.

*Flowers fragrance*.—Pleasantly and distinctly sweet.

*Petals*.—Four; glabrous; fused into salverform with typically straight cylindrical tube about 9.0 mm long and 2.0 mm diameter, and a flattened face about 10.0 mm across; petal blade rounded with crenate margin; blade to about 2.8 mm across and about 3.1 mm long from fused face; center flattened face portion of blade fused about 3.6 mm.

*Petal color*.—Adaxial center nearest RHS 11C in the tube surrounded by a thin irregular band of less than 0.7 mm width of between RHS 23A and RHS 21A, adaxial face blades nearest RHS N81A; abaxial tube nearest RHS 187B and abaxial petal blades nearest RHS N81B.

*Gynoecium*.—Pistil: one; about 3.0 mm long. Style: short, round, glabrous; about 2.0 mm long and less than 0.2 mm diameter; color nearest RHS 144C. Stigma: oblong, minutely puberulent; about 0.2 mm in diameter and less than 0.7 mm long; color nearest RHS 144B. Ovary: superior; globose; about 1.0 mm across at base and 1.0 mm tall; distally tapering to style; color between RHS 144A and RHS 144B.

*Androecium*.—Filaments: not produced or very short. Anthers: typically four; oblong; introrse; adnate to about mid-point of corolla tube; about 1.0 mm long and 0.5 mm wide; color nearest RHS 4D. Pollen: numerous, globose, less than 0.1 mm long; color nearest RHS 4D.

*Pedicel*.—Short, puberulent; about 2.0 mm long and about 0.5 mm diameter; color lighter than RHS N138D.

*Peduncle*.—Quadrangular, pubescent, flexible and strong; flowering portion to about 22.5 cm long.

*Peduncle color*.—Lighter than RHS N138D.

*Fruit*.—Moderate fruit set; oblong with acute apex; glabrous, bi-valved, septicidal capsule; about 8.0 mm long and about 2.0 mm diameter.

*Fruit color*.—As maturing nearest RHS 162D; when mature and dehiscing nearest RHS 164B.

*Seed*.—Elongated ellipse with sharply acute ends; less than about 2.0 mm long and about 0.1 mm diameter in center.

*Seed color*.—Nearest RHS 200A.

Disease resistance: Resistance has been noted to deer browsing. Other resistance beyond that of known butterfly bush cultivars has not been observed. The plant grows best with plenty of moisture and adequate drainage, but is able to tolerate some drought when mature. Hardiness at least from USDA zone 6 through 10.

*Buddleia* 'Dark Dynasty' has not been sold more than one year prior to filing the patent application. All disclosures have come either directly or indirectly from the inventor.

I claim:

1. A new cultivar of winter-hardy butterfly bush *Buddleia* plant named 'Dark Dynasty' as herein illustrated and described, especially suitable for potted plant culture, landscaping as a specimen or en masse or as cut flower purposes.

* * * * *